United States Patent
Whitten et al.

(10) Patent No.: US 8,753,570 B2
(45) Date of Patent: Jun. 17, 2014

(54) STRUCTURE, SYNTHESIS, AND APPLICATIONS FOR OLIGO PHENYLENE ETHYNYLENES

(75) Inventors: David Whitten, Albuquerque, NM (US); Yanli Tang, Xi'an (CN); Zhijun Zhou, Albuquerque, NM (US); Linnea Ista, Albuquerque, NM (US); Motokatsu Ogawa, Sherman Oaks, CA (US); David Keller, Albuquerque, NM (US); Brett Andrzejewski, Albuquerque, NM (US); Gabriel Lopez, Durham, NC (US); Kirk Schanze, Gainesville, FL (US)

(73) Assignee: STC.UNM, Albuquerque, NM (US)

( * ) Notice: Subject to any disclaimer, the term of this patent is extended or adjusted under 35 U.S.C. 154(b) by 595 days.

(21) Appl. No.: 13/001,478

(22) PCT Filed: Jun. 26, 2009

(86) PCT No.: PCT/US2009/048838
§ 371 (c)(1),
(2), (4) Date: May 11, 2011

(87) PCT Pub. No.: WO2009/158606
PCT Pub. Date: Dec. 30, 2009

(65) Prior Publication Data
US 2011/0223058 A1    Sep. 15, 2011

Related U.S. Application Data

(60) Provisional application No. 61/076,255, filed on Jun. 27, 2008.

(51) Int. Cl.
*A61L 2/00* (2006.01)
*A61L 2/18* (2006.01)
*A61L 9/00* (2006.01)
*C07C 239/00* (2006.01)
*C07C 259/00* (2006.01)

(52) U.S. Cl.
USPC .............. 422/28; 422/29; 564/300; 564/301

(58) Field of Classification Search
USPC ............................ 564/300, 301; 422/28, 29
See application file for complete search history.

(56) References Cited

FOREIGN PATENT DOCUMENTS

WO    WO-2009158606 A2    12/2009

OTHER PUBLICATIONS

George, W. N. et al. "Amplified fluorescence quenching in high ionic strength media". Soft Matter. 2007, vol. 3, pp. 1381-1387.*
Fan, Qu-Li et al. "Water-Soluble Cationic Poly(p-phenyleneethynylene)s (PPEs): Effects of Acidity and Ionic Strength on Optical Behavior". Macromolecules. 2005, vol. 38, pp. 2927-2936.*
European Application Serial No. 09771137.8, Office Action mailed Feb. 9, 2011, 1 pg.

(Continued)

*Primary Examiner* — Regina M Yoo
(74) *Attorney, Agent, or Firm* — Schwegman Lundberg & Woessner, P.A.

(57) ABSTRACT

Novel compounds generally referred to herein as cationic oligomeric phenylene ethynylenes (OPEs), methods of synthesizing OPEs and various uses for the OPEs are described. The compounds can be synthesized in both symmetrical (S-OPE) and non-symmetrical (N-OPE) forms. Suitable uses include sensor and biocidal applications. Reusable structures incorporating the OPEs that are able to capture and release biological species of interest are also described.

20 Claims, 10 Drawing Sheets

(56) References Cited

OTHER PUBLICATIONS

European Application Serial No. 09771137.8, Office Action mailed Feb. 14, 2011, 2 pgs.
European Application Serial No. 09771137.8, Office Action mailed Mar. 3, 2011, 1 pg.
European Application Serial No. 09771137.8, Office Action mailed Mar. 16, 2011, 1 pg.
European Application Serial No. 09771137.8, Response filed Feb. 18, 2011 to Office Action mailed Feb. 9, 2011, 6 pgs.
International Application Serial No. PCT/US2009/048838, International Preliminary Report on Patentability mailed Jan. 5, 2011, 7 pgs.
International Application Serial No. PCT/US2009/048838, International Search Report mailed Apr. 30, 2010, 4 pgs.
International Application Serial No. PCT/US2009/048838, Written Opinion mailed Apr. 30, 2010, 6 pgs.
Tang, Yanli, et al., "Synthesis, Self-Assembly, and Photophysical Behavior of Oligo Phenylene Ethynylenes: From Molecular to Supramolecular Properties", Langmuir vol. 25, (2009), 21-25.

* cited by examiner

STRUCTURE, SYNTHESIS, AND APPLICATIONS FOR OLIGO PHENYLENE ETHYNYLENES

STATEMENT REGARDING GOVERNMENT SPONSORED RESEARCH

This invention was made with Government support under HDTRA-1-07-0036 awarded by the Defense Threat Reduction Agency. The U.S. Government has certain rights in this invention.

CROSS-REFERENCE TO RELATED APPLICATIONS

The following application claims benefit of U.S. Provisional Application No. 61/076,255, filed Jun. 27, 2008, which is hereby incorporated by reference in its entirety.

BACKGROUND

The physical and photophysical properties of conjugated polymers and conjugated polyeletrolytes have been the subject of much recent investigation. See, e.g., Ober, C. K.; Wegner, G. Adv. Mater. 1997, 9, 17-31; Chen, L. H., McBranch, D. W., Wang, H. L., Helgeson, R., Wudl, F., and Whitten, D. G. Proc. Natl. Acad. Sci. U.S.A. 1999 96 12287 12292; Peyratout, C. S., and Dahne, L. Angew. Chem., Int. Ed. 2004 43 3762 3783; Haskins-Glusac, K., Pinto, M. R., Tan, C. Y., and Schanze, K. S. J. Am. Chem. Soc. 2004 126 14964 14971; and Handbook of Conducting Polymers. Conjugated Polymers: Processing and Applications, 3rd ed.; Skotheim, T. A., and Reynolds, J. R., Eds.; CRC Press: Boca Raton, Fla., 2007, each of which is hereby incorporated by reference. In most cases, these compounds are prepared by synthesis procedures that do not permit the rigorous control of polymer chain length, and the macromolecules may consist of a mixture of molecules with a broad range of molecular weights. See, e.g., Roncali, J. Chem. Rev. 1997 97 173 205; Pinto, M. R., and Schanze, K. S. Synthesis 2002 1293 1309; and Yamamoto, T. Synlett 2003 425 450, each of which is incorporated by reference. Accordingly, novel synthesis methods that allow for precise control of polymer chain length and which result in the generation of population of molecules having a narrow range of molecular weights is desirable for a wide variety of applications.

DETAILED DESCRIPTION

The present disclosure provides a plurality of novel compounds generally referred to herein as cationic oligomeric phenylene ethynylenes (OPEs), methods of synthesizing OPEs and various uses for the OPEs. The OPEs described herein can generally be divided into two different classes, non-symmetrical (N-OPEs) and symmetrical (S-OPEs).

Figure 1:
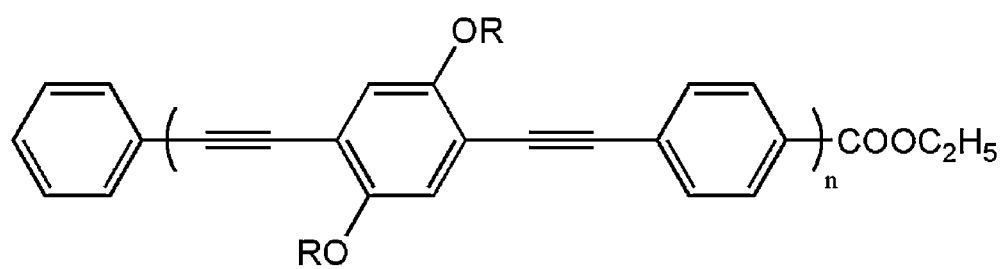
FIG. 1 depicts the basic structure of an OPE according to an embodiment of the present disclosure.

According to an embodiment, the present disclosure provides non-symmetrical cationic oligomeric phenylene ethynylenes (N-OPEs) having the structure shown in FIG. 1, where n ranges from 1 to 10 (referred to separately as N-OPE-1, N-OPE-2, N-OPE-3, etc.). The N-OPE shown in FIG. 1 can be studied in solution, in colloidal suspensions, and attached, for example, by modification of the carboxyester "headgroup," to surfaces by various covalent linkages.

Figure 2:
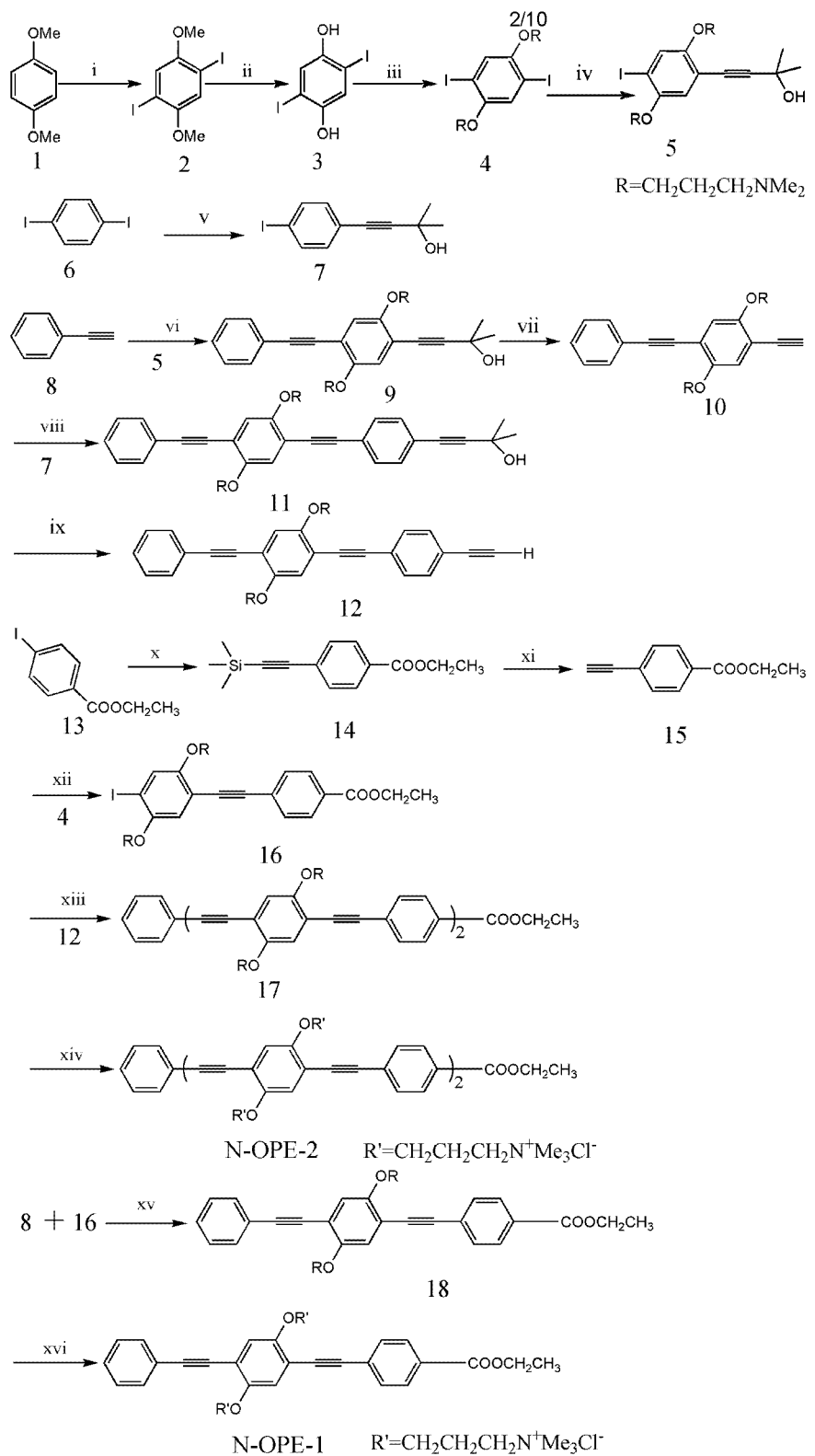
FIG. 2 depicts the multistep synthesis procedure for various OPEs, according to the present disclosure.

Synthesis of the N-OPE units shown in FIG. 1 can be carried out by a multistep procedure as outlined in FIG. 2. Viewing FIG. 2, 4-(4-iodophenyl)-2-methylbut-3-yn-2-ol (compound 4) and 1,4-Bis((3-(dimethylamino)propyl)oxy)-2,5-diiodobenzene (compound 7) were prepared according to the literature procedure. See e.g., Goeb, S.; Ziessel, R. Org. Lett. 2007, 9, 737-740 and Weder, C.; Wrighton, M. S. Macromolecules 1996, 29, 5157-5165, each of which is incorporated by reference.

Synthesis of compound 5 is as follows: Compound 4 (8.0 g, 15 mmol) was dissolved in $Et_2NH$ (72 mL) and $CHCl_3$ (120 mL) then the solution was degassed with nitrogen for 30 min. $Pd[PPh_3]_2Cl_2$ (210 mg, 2%) and CuI (115 mg, 4%) were added into the solution followed by addition of 2-methyl-3-butyn-2-ol (1.26 g, 15 mmol) dropwise. After stirring the reaction mixture for 5 h at room temperature, a saturated aqueous $NH_4Cl$ solution was added into the solution. The aqueous phase was extracted with $CH_2Cl_2$ twice. The combined organic layer was dried over anhydrous $MgSO_4$. The solvents were removed under reduced pressure. The residue was purified by column chromatography (silica gel, $CH_2Cl_2$—$CH_3OH$, 100:1~50:1 with 0.5% triethylamine v/v) to afford compound 5 as pale-yellow solid (3.51 g, 48%): $^1H$ NMR (500 MHz, $CDCl_3$): δ=7.27 (s, 2H), 6.80 (s, 2H), 3.99 (m, 4H), 2.53 (m, 4H), 2.27 (s, 12H), 1.98 (m, 4H), 1.61 (s, 6H). $^{13}C$ NMR (125 MHz, $CDCl_3$) δ 155.0, 152.5, 125.5, 116.6, 114.5, 100.2, 87.7, 78.2, 69.2 68.6, 65.5, 57.0, 56.8, 46.1, 45.9, 32.2, 28.2, 27.9. MS (EI) (m/z) 489 ([M+H]$^+$, 100%)

Synthesis of compound 9 is as follows: The solution of 8 (1.94 g, 4 mmol) and 5 (490 mg, 4.8 mmol) in $Et_2NH$ (45 mL) and $CHCl_3$ (45 mL) was degassed under nitrogen for 30 min. $Pd[PPh_3]_2Cl_2$ (56 mg, 2%) and CuI (31 mg, 4%) were added into the solution. After stirring the reaction mixture for 3 h at room temperature, a saturated aqueous $NH_4Cl$ solution was added into the solution. The aqueous phase was extracted with $CH_2Cl_2$ twice. The combined organic layer was dried over anhydrous $MgSO_4$. The solvents were removed under reduced pressure. The residue was purified by column chromatography (silica gel, $CH_2Cl_2$—$CH_3OH$, 50:1 with 0.5% triethylamine v/v) to afford compound 9 as light-yellow solid (1.55 g, 84%): $^1H$ NMR (500 MHz, $CDCl_3$): δ=7.52 (m, 2H), 7.33 (m, 3H), 7.00 (s, 1H), 6.91 (s, 1H), 4.05 (t, J=6.0 Hz, 4H), 2.54 (m, 4H), 2.27 (s, 6H), 2.24 (s, 6H), 2.00 (m, 4H), 1.62 (s, 6H). $^{13}C$ NMR (125 MHz, $CDCl_3$) δ 154.3, 132.1, 128.9, 124.0, 118.5, 117.6, 114.7, 114.4, 100.8, 95.3, 86.3, 78.6, 68.9, 68.4, 65.4, 57.0, 56.9, 46.0, 45.9, 32.2, 28.2, 28.1. MS (EI) (m/z) 463 ([M+H]$^+$, 100%)

Synthesis of compound 10 is as follows: Compound 9 (1.1 g, 2.4 mmol) and potassium tert-butoxide (550 mg, 4.8 mmol) were added into anhydrous tert-butyl alcohol (25 mL). After refluxing under nitrogen for 3 h, the resultant dark-red mixture was cooled and then water was added into the solution. The aqueous phase was extracted with $CH_2Cl_2$ for three times. The solvent was removed under reduced pressure. The residue was purified by column chromatography (silica gel, $CH_2Cl_2$—$CH_3OH$, 100:1-50:1 with 0.5% triethylamine v/v) to afford 10 as red-yellow oil which turned into an amorphous solid upon standing. (1.15 g, 48%): $^1H$ NMR (500 MHz, $CDCl_3$): δ=7.52 (m, 2H), 7.33 (m, 3H), 7.01 (s, 1H), 6.98 (s, 1H), 4.06 (m, 4H), 3.33 (s, 1H), 2.54 (m, 4H), 2.28 (s, 6H), 2.26 (s, 6H), 2.02 (m, 4H). $^{13}C$ NMR (125 MHz, $CDCl_3$) δ 154.8, 154.0, 132.2, 129.0, 124.0, 118.6, 117.7, 115.4, 113.3, 95.7, 86.2, 83.1, 80.6, 68.5, 57.1, 56.9, 46.0, 28.1, 27.9. (EI) (m/z) 405 ([M+H]$^+$, 100%), 203 ([M+2H]$^+$, 60%).

Synthesis of compound 11 is as follows: By analogy to the synthesis of compound 9, compound 10 (566 mg, 1.4 mmol), compound 7 (440 mg, 1.54 mmol, 1.1 equiv), $Pd[PPh_3]_2Cl_2$ (11 mg), CuI (6 mg), $Et_2NH$ (10 mL), and $CHCl_3$ (10 mL), at room temperature for 3 h to yield compound 11 as a yellow solid (588 mg, 79%) after column chromatography (silica gel, $CH_2Cl_2$—$CH_3OH$, 40:1 with 0.5% triethylamine v/v). $^1H$ NMR (500 MHz, $CDCl_3$): δ=7.52 (m, 2H), 7.46 (d, J=8.0 Hz, 2H), 7.39 (d, J=8.0 Hz, 2H), 7.33 (m, 3H), 7.03 (s, 1H), 7.01 (s, 1H), 4.08 (t, J=6.0 Hz, 4H), 2.58 (m, 4H), 2.27 (s, 12H), 2.04 (m, 4H), 1.62 (s, 6H). $^{13}C$ NMR (125 MHz, $CDCl_3$) δ 153.5, 131.5, 131.3, 128.3, 123.2, 123.0, 122.8, 116.9, 114.2, 113.6, 96.4, 95.0, 94.4, 87.5, 85.7, 81.3, 67.7, 64.9, 56.3, 45.9, 45.3, 31.5, 27.2. (EI) (m/z) 563 ([M+H]$^+$, 90%), 282 ([M+2H]$^+$, 100%).

Synthesis of compound 12 is as follows: By analogy to the synthesis of compound 10, compound 11 (390 mg, 0.7 mmol), potassium tert-butoxide (161 mg, 1.4 mmol), and tert-butyl alcohol (8 mL), refluxing for 3 h to yield compound 12 as a red-yellow oil which turned into an amorphous solid upon standing. (158 mg, 45%) after column chromatography (silica gel, $CH_2Cl_2$—$CH_3OH$, 40:1 with 0.5% triethylamine v/v). $^1H$ NMR (500 MHz, $CDCl_3$): δ=7.53 (m, 2H), 7.47 (m, 4H), 7.34 (m, 3H), 7.03 (s, 1H), 7.02 (s, 1H), 4.09 (t, J=6.0 Hz, 4H), 2.55 (m, 4H), 2.26 (s, 12H), 2.03 (m, 4H). (EI) (m/z) 505 ([M+H]+, 100%), 253 ([M+2H]$^+$, 80%)

Synthesis of compound 14 is as follows: By analogy to the synthesis of compound 9, compound 13 (5.5 g, 20 mmol), (trimethylsilyl)acetylene (2.2 g, 22 mmol, 1.1 equiv), $Pd[PPh_3]_2Cl2$ (420 mg), CuI (230 mg), THF (80 mL), and diisopropylamine (40 mL), at room temperature for 17 h to yield compound 14 as a red-yellow oil (4.77 g, 97%) after column chromatography (silica gel, $CH_2Cl_2$-hexane, 1:2 v/v). $^1H$ NMR (500 MHz, CDCl3): δ=7.98 (d, J=8.5 Hz, 2H), 7.52 (d, J=8.0 Hz, 2H), 4.38 (m, 2H), 1.39 (t, J=7.0 Hz, 3H). 0.26 (s, 9H). $^{13}C$ NMR (125 MHz, $CDCl_3$) δ 166.0, 132.2 130.5, 129.7, 128.1, 104.7, 97.7, 61.3, 14.7, 0.25. MS (EI) (m/z) 269 ([M+Na]$^+$, 100%)

Synthesis of compound 15 is as follows: A mixture of compound 14 (3.7 g, 15 mmol) and $K_2CO_3$ (4.14 g, 30 mmol) in ethanol (500 mL) was degassed with nitrogen for 30 min The mixture solution was stirred at room temperature for 4 h. After removing the solvent, the residue was treated with water and $CH_2Cl_2$. The aqueous phase was extracted with $CH_2Cl_2$ twice. The combined organic layer was dried over anhydrous $MgSO_4$. The solvents were removed under reduced pressure to obtain compound 14 as red-yellow oil (2.35 g, 90%). No further purification was necessary. $^1H$ NMR (500 MHz, $CDCl_3$): δ=8.00 (d, J=8.5 Hz, 2H), 7.55 (d, J=8.5 Hz, 2H), 4.38 (m, 2H), 3.22 (s, 1H), 1.39 (t, J=8.0 Hz, 3H). $^{13}C$ NMR (125 MHz, $CDCl_3$) δ 166.3, 132.5 131.0, 130.0, 127.1, 83.3, 80.6, 61.6, 14.8.

Synthesis of compound 16 is as follows: By analogy to the synthesis of 5, compound 4 (1.86 g, 3.5 mmol), compound 15 (610 mg, 3.5 mmol), $Pd[PPh_3]_2Cl_2$ (25 mg), CuI (13 mg), $Et_2NH$ (30 mL), and $CHCl_3$ (30 mL), at room temperature for 2 h to yield compound 16 as a yellow solid (390 mg, 94%) after column chromatography (silica gel, $CH_2Cl_2$—$CH_3OH$, 40:1~10:1 v/v). $^1H$ NMR (500 MHz, $CDCl_3$): δ=8.03 (d, 2H, J=8.0 Hz), 7.58 (d, 2H, J=8.0 Hz), 7.34 (s, 1H), 6.94 (s, 1H), 4.39 (m, 2H), 4.04 (m, 4H), 2.53 (m. 4H), 2.28 (s, 6H), 2.25 (s, 6H), 2.01 (m, 4H), 1.40 (t, J=7.5 Hz, 3H). $^{13}C$ NMR (125 MHz, $CDCl_3$) δ 166.6, 155.0, 152.4, 131.9, 130.5, 130.1, 128.5, 124.5, 116.6, 113.6, 94.1, 89.1, 88.9, 68.7, 68.6, 61.7, 56.9, 46.0, 45.9, 28.0, 27.8, 14.9. MS (EI) (m/z) 579 ([M+H]$^+$, 100%).

Synthesis of compound 17 is as follows: By analogy to the synthesis of compound 9, compound 12 (136 mg, 0.27 mmol), compound 16 (156 mg, 0.27 mmol), $Pd[PPh_3]_2Cl_2$ (4 mg), CuI (2 mg), $Et_2NH$ (4 mL), and $CHCl_3$ (4 mL), at room temperature for 6 h to yield compound 17 as a yellow solid (124 mg, 48%) after column chromatography (silica gel, $CH_2Cl_2$—$CH_3OH$, 10:1 with 0.5% triethylamine v/v). $^1H$ NMR (500 MHz, $CDCl_3$): δ=8.00 (d, 2H, J=7.5 Hz), 7.67 (d, 2H, J=7.5 Hz), 7.59 (s, 4H), 7.53 (m, 2H), 7.43 (m, 3H), 7.25-7.20 (m, 4H), 4.32 (m, 2H), 4.10 (m, 8H), 2.74 (m, 8H), 2.38 (s, 24H), 2.00 (m, 8H), 1.30 (t, 3H, J=7.5 Hz). $^{13}C$ NMR (125 MHz, $CDCl_3$) δ 166.2, 153.9, 153.7, 132.7, 131.7, 131.6, 130.1, 129.7, 128.6, 128.3, 128.1, 123.5, 117.3, 114.6, 113.9, 95.4, 95.2, 94.8, 94.5, 88.9, 88.1, 88.0, 86.0, 68.0, 61.3, 56.6, 45.4, 29.9, 27.5, 14.5. MS (EI) (m/z) 955 ([M+H]$^+$, 100%)

Synthesis of compound 18 is as follows: By analogy to the synthesis of compound 9, compound 16 (434 mg, 0.75 mmol), compound 8 (92 mg, 0.9 mmol, 1.2 equiv), $Pd[PPh_3]_2Cl_2$ (20 mg), CuI (11 mg), $Et_2NH$ (8 mL), and $CHCl_3$ (8 mL), at room temperature for 3 h to yield compound 18 as a yellow solid (390 mg, 94%) after column chromatography (silica gel, CH$_2$Cl$_2$—CH$_3$OH, 10:1 with 0.5% triethylamine v/v). $^1$H NMR (500 MHz, CDCl$_3$): δ=8.04 (d, 2H,), 7.59 (d, 2H, J=8.0 Hz), 7.55 (d, 2H, J=7.5 Hz), 7.36 (m, 3H), 7.05 (s, 2H), 4.40 (m, 2H), 4.10 (t, 4H, J=6.0 Hz), 2.60 (m. 4H), 2.29 (s, 12H), 2.06 (m, 4H), 1.41 (t, 3H, J=7.0 Hz). $^{13}$C NMR (125 MHz, CDCl$_3$) δ 166.5, 154.2, 154.0, 132.0, 131.8, 130.3, 130.0, 128.8, 128.5, 123.8, 117.6, 117.4, 115.2, 113.8, 95.7, 94.6, 89.3, 86.2, 68.3, 68.2, 61.6, 56.9, 46.0, 45.9, 28.0, 14.8. (EI) (m/z) 553 ([M+H]$^+$, 90%), 277 ([M+2H]$^+$, 100%).

Synthesis of N-OPE-1 is as follows: To a solution of compound 18 (276 mg, 0.5 mmol) in CH$_2$Cl$_2$ (8 mL) was added excess iodomethane (1.4 g, 10 mmol). After stiffing the reaction mixture for 4 h at room temperature, the precipitate was isolated and washed with CH$_2$Cl$_2$. The solid was dissolved in an excess of acetone and precipitated by addition of an excess of tetrabutylammonium chloride. The N-OPE-1 was obtained as a light-yellow solid (325 mg, 93%) by suction filtration. $^1$H NMR (500 MHz, DMSO-d6): δ=8.03 (d, J=8.0 Hz, 2H), 7.70 (d, J=8.0 Hz, 2H), 7.57 (m, 2H), 7.47 (m, 3H), 7.33 (s, 1H), 7.28 (s, 1H), 4.35 (m, 2H), 4.17 (m, 4H), 3.50 (m, 4H), 3.10 (s, 9H), 3.09 (s, 9H), 2.25 (m, 4H), 1.34 (t, J=7.0 Hz, 3H). MS (EI) (m/z) 291 (M+, 100%)

Synthesis of N-OPE-2 is as follows: By analogy to the synthesis of N-OPE-1, 17 (72 mg, 0.075 mmol) and CH$_2$Cl$_2$ (3 mL), at room temperature for 4 h to yield N-OPE-2 as a yellow solid (40 mg, 45%) by suction filtration. $^1$H NMR (500 MHz, DMSO-d6): δ=8.01 (d, J=7.0 Hz, 2H), 7.69 (d, J=7.5 Hz, 2H), 7.63 (s, 4H), 7.55 (m, 2H), 7.44 (m, 3H), 7.33-7.25 (m, 4H), 4.33 (m, 2H), 4.15 (m, 8H), 3.50 (m, 8H), 3.15-3.11 (m, 36H), 2.24 (m, 8H), 1.30 (t, 3H, J=7.5 Hz). 1.34 (t, J=7.0 Hz, 3H).

N-OPE-3 through N-OPE-10 are formed by analogy to the formation of N-OPE-1 and N-OPE-2 using the appropriate intermediates in order to form longer chain compounds. For example, N-OPE-3 is formed by reacting iterations of steps vi-viii and subsequent reaction of the longer chain compounds with compound 16.

Figure 3:
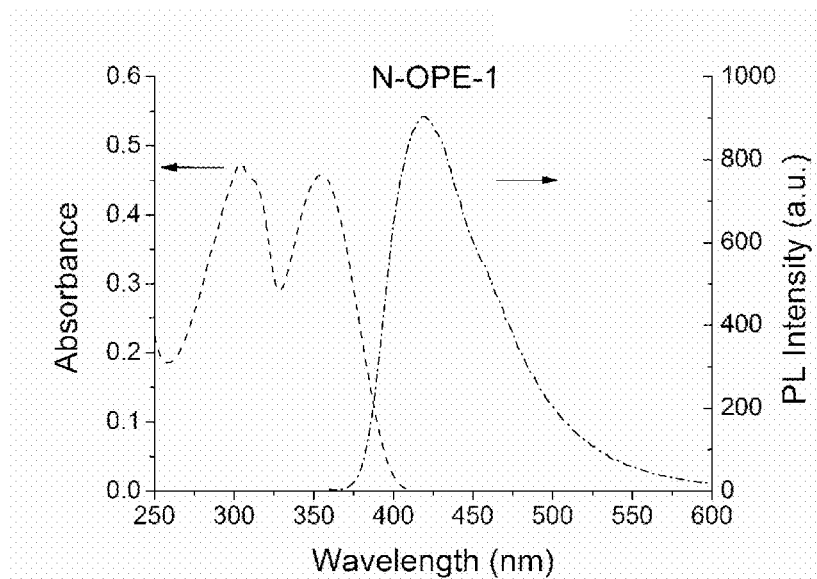
FIG. 3 shows absorption and fluorescence spectra for N-OPE-1 in water.
Figure 4:
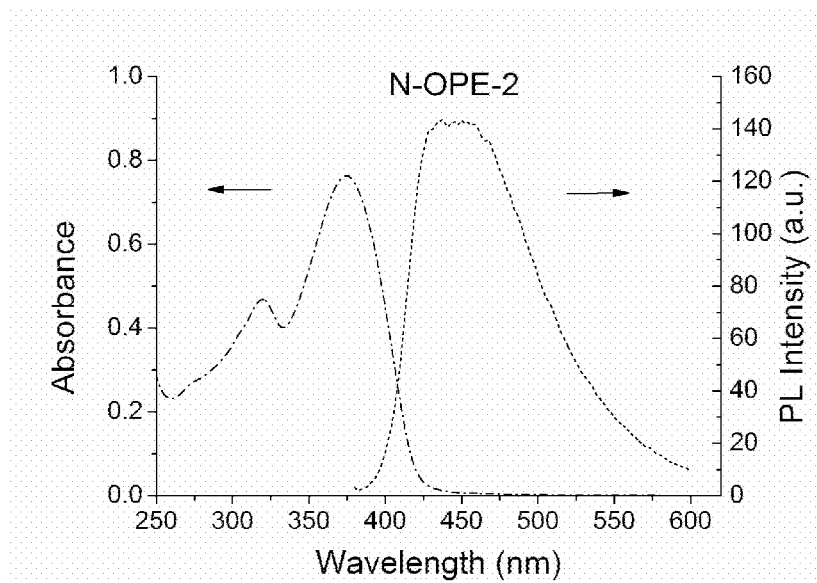
FIG. 4 shows absorption and fluorescence spectra for N-OPE-2 in water.

While the synthetic steps are all straight-forward, those involving conversion of the diiodobenzene to 4-(4-iodophenyl)-2-methyl-3-butyn-2-ol occur with lower yields and the desired products must be separated from structurally similar byproducts. The alkylamino groups were attached in an early step but converted to the quaternary ammonium derivatives as the last step of the synthesis. The intermediates and final products were characterized by mass spectrometry and proton and carbon NMR. N-OPE-1 and N-OPE-2 are readily soluble in water and polar organic solvents such as methanol. Absorption and fluorescence spectra for N-OPE-1 in water are shown in FIG. 3. Absorption and fluorescence spectra for N-OPE-2 in water are shown in FIG. 4. Table 1 gives quantum efficiencies for fluorescence and fluorescence lifetimes.

TABLE 1

Quantum Yields and fluorescence lifetimes of N-OPE-1 and N-OPE-2

| Compound | Solvent | $\Phi_f$ | $\tau_f$ (ns) |
| --- | --- | --- | --- |
| N-OPE-1 | H$_2$O | 0.147 | 0.78 |
|  | Methanol | 0.68 | 1.57 |
| N-OPE-2 | H$_2$O | 0.012 | 0.37 |
|  | Methanol | 0.68 | 0.92 |

The absorption and fluorescence in methanol occur at very similar wavelengths. In both solvents there is no concentration dependence of the spectra in the micromolar range and it seems likely that in both solvents the N-OPE are monomeric. While N-OPE-1 and N-OPE-2 both exhibit high fluorescence quantum efficiencies in methanol (quinine sulfate was used as a standard), the fluorescence is much weaker for both compounds in water with N-OPE-1 having a quantum efficiency of ~15% and N-OPE-2 having an efficiency of just over 1%. Fluorescent lifetimes in water are correspondingly shorter than in methanol.

Figure 5:
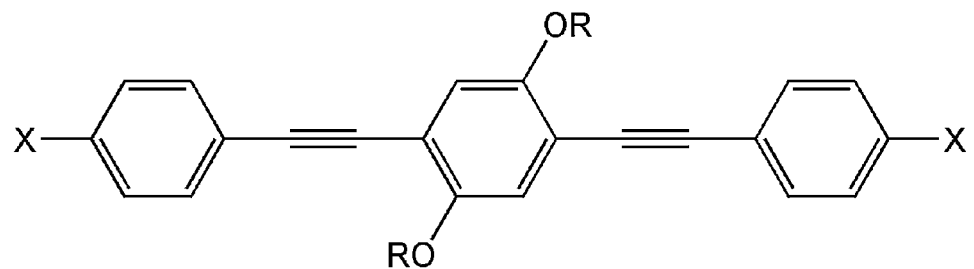
FIG. 5 depicts the basic structure of an S-OPE according to an embodiment of the present disclosure.

According to another embodiment, the present disclosure provides symmetrical cationic oligophenylene ethynylenes (S-OPEs). One exemplary embodiment is the S-OPE-n-x family shown in FIG. 5, where n is a number between 1 and 10 and x is H, CO$_2$Et, COO$^-$, NH$_2$ or COCH$_3$ (referred to separately as S-OPE-n (H), S-OPE-n (CO$_2$Et), S-OPE-n (COO$^-$), S-OPE-n (NH$_2$), and S-OPE-n (COCH$_3$). Because the symmetrical molecules can be built by adding the same unit to both sides of a symmetrical diiodobenzene derivative, the synthesis of the symmetrical molecules is much simpler than the synthesis of the unsymmetrical OPEs.

Figure 6:
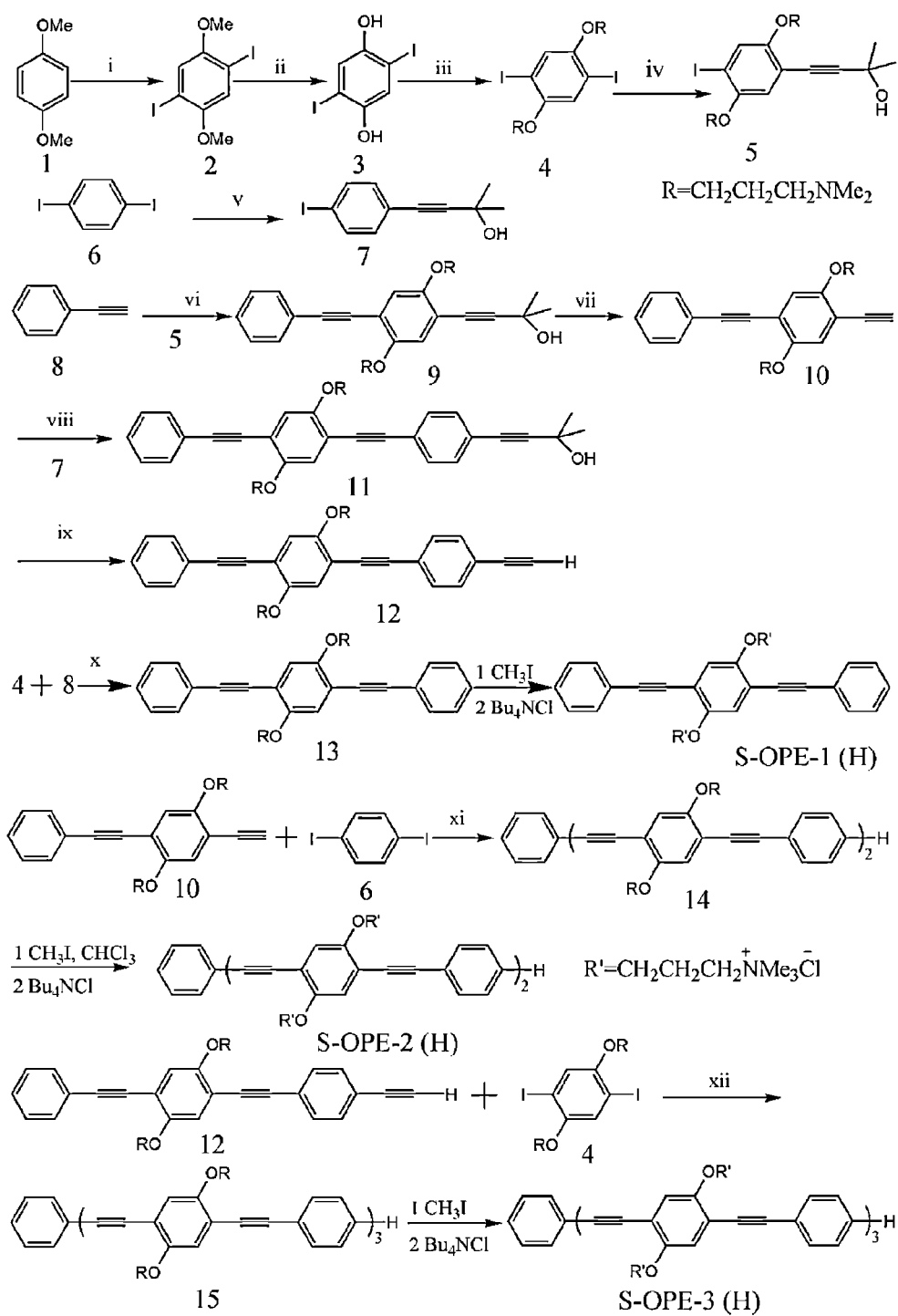
FIG. 6 depicts the multistep synthesis procedure for an S-OPE, according to the present disclosure.

An exemplary synthesis method for the S-OPE-n (H) family (where n=1, 2, or 3) can be carried out by a multi-step process as shown in FIG. 6. As shown, compounds 1-12 are identical to those shown in the N-OPE-n synthesis method shown in FIG. 2.

Synthesis of compound 13 is as follows: By analogy to the synthesis of compound 9, compound 4 (532 mg, 1.0 mmol), compound 8 (245 mg, 2.4 mmol, 1.2 equiv), Pd[PPh$_3$]$_2$Cl$_2$ (28 mg), CuI (15 mg), Et$_2$NH (10 mL), and CHCl$_3$ (10 mL), at room temperature for 6 h to yield compound 13 as a yellow solid (336 mg, 70%) after column chromatography (silica gel, CH$_2$Cl$_2$—CH$_3$OH, 50:1 with 0.5% triethylamine v/v). $^1$H NMR (500 MHz, CDCl$_3$): δ=7.53 (d, J=8.0 Hz, 4H), 7.34 (m, 6H), 7.04 (s, 2H), 4.09 (t, J=6.0 Hz, 4H), 2.54 (t, J=7.0 Hz, 4H), 2.25 (s, 12H), 2.02 (m, 4H). $^{13}$C NMR (125 MHz, CDCl$_3$) δ 153.7, 131.7, 128.5, 128.4, 123.6, 117.2, 114.2, 95.0, 86.0, 68.0, 56.6, 45.7, 27.8.

Synthesis of compound 14 is as follows: By analogy to the synthesis of compound 9, compound 6 (84 mg, 0.25 mmol), compound 10 (242 mg, 0.6 mmol, 1.2 equiv), Pd[PPh$_3$]$_2$Cl$_2$ (7 mg), CuI (4 mg), Et$_2$NH (4 mL), and CHCl$_3$ (8 mL), at room temperature for 6 h to yield compound 14 as a yellow solid (145 mg, 65%) after column chromatography (silica gel, CH$_2$Cl$_2$—CH$_3$OH, 20:1 with 0.5% triethylamine v/v). $^1$H NMR (500 MHz, CDCl$_3$): δ=7.53 (m, 4H), 7.51 (s, 4H), 7.34 (m, 6H), 7.05 (s, 2H), 7.04 (s, 2H), 4.10 (m, 8H), 2.55 (m, 8H), 2.26 (s, 24H), 2.03 (m, 8H). $^{13}$C NMR (125 MHz, CDCl$_3$) δ 154.2, 154.1, 132.1, 132.0, 129.0, 123.9, 123.8, 117.5, 114.8, 114.2, 95.6, 95.1, 88.4, 86.3, 68.4, 56.9, 46.0, 28.1.

Synthesis of compound 15 is as follows: By analogy to the synthesis of compound 9, compound 4 (134 mg, 0.25 mmol), compound 12 (302 mg, 0.6 mmol, 1.2 equiv), Pd[PPh$_3$]$_2$Cl$_2$ (7 mg), CuI (4 mg), Et$_2$NH (4 mL), and CHCl$_3$ (10 mL), at room for 6 h to yield compound 15 as a yellow solid (192 mg, 60%) after column chromatography (silica gel, CH$_2$Cl$_2$—CH$_3$OH, 5:1 with 0.5% triethylamine v/v). $^1$H NMR (500 MHz, CDCl$_3$): δ=7.53 (m, 4H), 7.51 (s, 8H), 7.34 (m, 6H), 7.05 (s, 6H), 4.10 (m, 12H), 2.55 (m, 12H), 2.27 (s, 36H), 2.04 (m, 12H). $^{13}$C NMR (125 MHz, CDCl$_3$) δ 154.1, 132.1, 132.0, 128.8, 123.9, 123.8, 123.7, 117.5, 114.8, 114.5, 114.2, 95.6, 95.3, 95.1, 88.5, 88.4, 86.4, 68.4, 60.0, 46.1, 28.1.

Synthesis of S-OPE-1(H) is as follows: By analogy to the synthesis of N-OPE-1, 13 (106 mg, 0.22 mmol) and CH$_2$Cl$_2$ (6 mL), at room temperature for 4 h to yield S-OPE-1(H) as a yellow solid (112 mg, 88%) by suction filtration. $^1$H NMR (500 MHz, DMSO-d6): δ=7.56 (m, 4H), 7.46 (m, 6H), 7.28 (s, 2H), 4.15 (t, J=6.0 Hz, 4H), 3.50 (m, 4H), 3.08 (s, 18H), 2.24 (m, 4H).

Synthesis of S-OPE-2(H) is as follows: By analogy to the synthesis of N-OPE-1, 14 (124 mg, 0.14 mmol) and CH$_2$Cl$_2$ (15 mL), at room temperature for 4 h to yield S-OPE-2(H) as a yellow solid (110 mg, 73%) by suction filtration. $^1$H NMR (500 MHz, DMSO-d6): δ=7.64 (s, 4H), 7.57 (m, 4H), 7.46 (b, 6H), 7.31 (s, 2H), 7.29 (s, 2H), 4.16 (m, 8H), 3.51 (m, 8H), 3.12 (s, 18H), 3.10 (s, 18H), 2.26 (b, 8H).

Synthesis of S-OPE-3(H) is as follows: By analogy to the synthesis of N-OPE-1, 15 (124 mg, 0.096 mmol) and $CH_2Cl_2$ (20 mL), at room temperature for 4 h to yield S-OPE-3(H) as a yellow solid (130 mg, 85%) by suction filtration. $^1$H NMR (500 MHz, DMSO-d6): δ=7.65 (b, 4H), 7.57 (b, 8H), 7.47 (b, 6H), 7.31-7.29 (m, 6H), 4.18 (m, 12H), 3.52 (m, 12H), 3.19-3.09 (b, 54H), 2.27 (b, 12H).

Three symmetrical molecules, S-OPE-1 (H), S-OPE-1 (COOEt) and S-OPE-1 (COO—) show similar two-banded absorption spectra in water and methanol. The absorption and fluorescence maxima for N-OPE-1 and the three S-OPE-1 compounds identified above are listed in Table 2.

TABLE 2

Fluorescence quantum efficiencies and lifetimes

| | Abs. (nm) | Em. (nm) | $\phi_f$ in $H_2O$ | τ (ns) | $\tau_{T4}$ (µs) | $\phi_f$ in $CH_3OH$ | τ (ns) |
|---|---|---|---|---|---|---|---|
| N—OPE-1 | 303, 355 | 420 | 0.15 ± 0.018 | 1.5 | 107 | 0.68 ± 0.028 | 1.6 |
| S—OPE-1 (H) | 303, 348 | 496 | 0.80 ± 0.011 | 1.6 | 216 | 0.82 ± 0.030 | 1.4 |
| S—OPE-1 (COO$^-$) | 310, 355 | 422 | 0.70 ± 0.010 | 1.5 | 136 | 0.74 ± 0.042 | 1.3 |
| S—OPE-1 (COOEt) | 314, 362 | 465 | 0.023 ± 0.001 | 1.0 | 77 | 0.75 ± 0.019 | 1.4 |

The spectra are concentration independent in the micromolar concentration range and there is a small red shift in the series: S-OPE-1 (H), N-OPE-1=S-OPE-1 (COO—), S-OPE-1 (COOEt). Each of the compounds also exhibits a relatively broad structureless single fluorescence transition in the range 380-450 nm for both methanol and aqueous solutions. Furthermore, we have also synthesized and carried out studies of S-OPE-1 (x) where x=$NH_2$, $COCH_3$, both of these compounds show similar absorption spectra to that of S-OPE-1 (COOEt). The fluorescence of all four compounds shown in Table 2 is strong in methanol and there is little variation in fluorescence efficiency among the different substituted derivatives. However there is a significant variation in the fluorescence efficiencies in aqueous solution ranging from 0.02 for S-OPE-1 (COOEt) to 0.80 for S-OPE-1 (H). While the diester derivative S-OPE-1 (COOEt) shows a very low fluorescence quantum efficiency in water, the dicarboxylate derivative shows very strong fluorescence in aqueous solution near neutral pH. Clearly the ester groups in N-OPE-1 and S-OPE-1 (COOEt) must play a major role in a solvent-dependent process which deactivates the excited singlet of the oligomers in water. Nanosecond transient absorption spectroscopy was carried out on the OPEs in order to monitor the triplet states. For all four compounds in aqueous solution transients giving rise to broad transient absorption bands were observed in the mid-visible region with lifetimes in the microsecond range (Table 2). The transient lifetimes and spectra are consistent with a triplet state assignment. The lmax of triplet-triplet absorption shifts from 518 nm to 569 nm following the extent of conjugation: S-OPE1-H (518 nm), N-OPE-1 (533 nm), S-OPE-1 (COO—) (557 nm), then S-OPE-1 (COOEt) (569 nm). The apparent triplet yields decrease in the order of S-OPE-1 (H)>S-OPE-1 (COO—)>>N-OPE-1>>S-OPE-1 (COOEt). The triplet lifetimes follow a similar trend as the triplet yield (Table 2). Interestingly, the relatively low triplet yield for S-OPE-1 (COOEt) mirrors the low fluorescence quantum yield, suggesting that the triplet formation is suppressed by the same mechanism that quenches the singlet state.

Figure 7:
FIG. 7 shows the structure of an exemplary S-OPE-1-EO.
Figure 8:
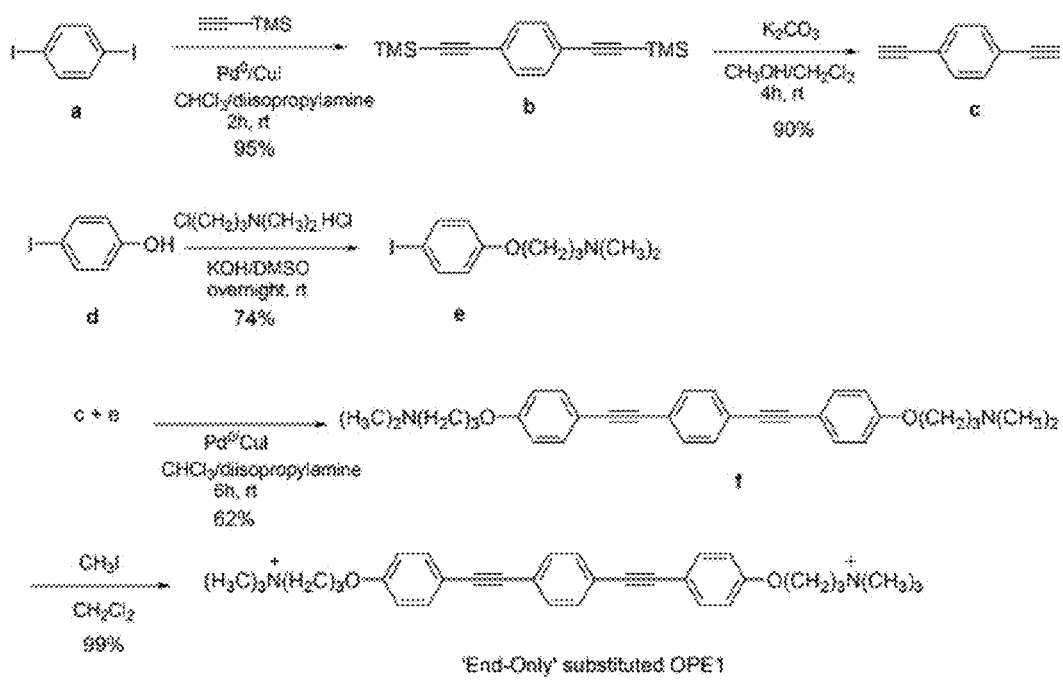
FIG. 8 provides an exemplary synthesis scheme for the S-OPE-1-EO shown in FIG. 7.

According to yet another embodiment, the present disclosure provides a symmetrical cationic oligophenylene ethynylenes that includes cationic groups at both ends of the OPE chain, but not in the middle. An exemplary embodiment is the S-OPE-1-EO shown in FIG. 7. An exemplary synthesis scheme for S-OPE-1-EO is shown in FIG. 8.

According to still another embodiment, the present disclosure provides dimers or large aggregates of the presently disclosed compounds. According to an example, the presently-described compounds are allowed to self-assemble on an anionic scaffold such as carboxymethylcellulose (CMC), carboxymethylamylose (CMA) or Laponite clay.

It has been previously determined that several cationic cyanine dyes self-assemble on CMC, CMA and Laponite clay to form J-aggregates characterized by sharp red-shifted bands in both absorption and fluorescence spectra. See e.g., Jones, R. M.; Bergstedt, T. S.; Buscher, C. T.; McBranch, D.; Whitten, D. Langmuir 2001, 17, 2568-2571; Lu, L. D.; Jones, R. M.; McBranch, D.; Whitten, D. Langmuir 2002, 18, 7706-7713; Kim, O. K.; Je, J.; Jernigan, G.; Buckley, L.; Whitten, D. J. Am. Chem. Soc. 2006, 128, 510-516; and Whitten, D. G.; Achyuthan, K. E.; Lopez, G. P.; Kim, O. K. Pure Appl. Chem. 2006, 78, 2313-2323, each of which is incorporated by reference. All three of these materials are transparent in the near uv where the OPE absorb and aggregation should be easily followed by changes in absorption and/or fluorescence spectra.

Figure 9:
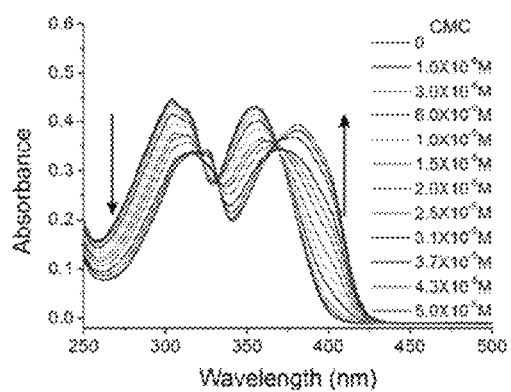
FIG. 9 shows the absorption spectra of N-OPE-1 upon addition of various CMC concentrations.
Figure 10:
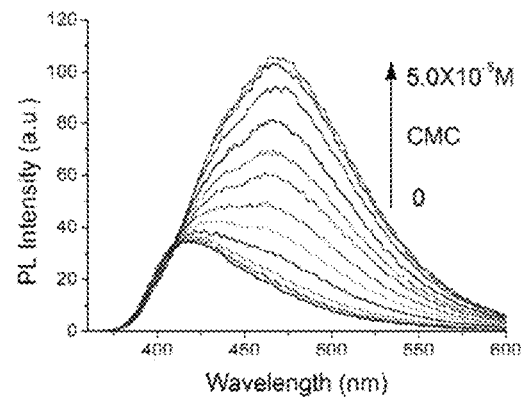
FIG. 10 shows the fluorescence spectra of N-OPE-1 upon addition of CMC.
Figure 11:
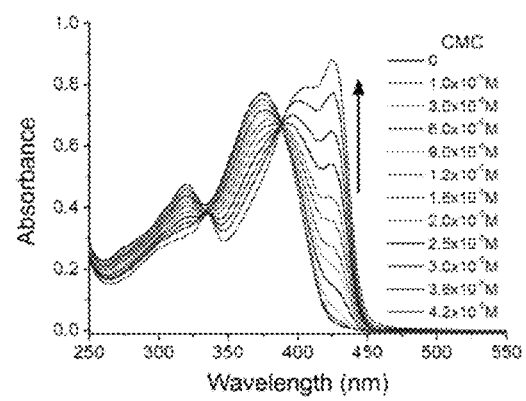
FIG. 11 shows the absorption spectra for N-OPE-2 upon addition of CMC.
Figure 12:
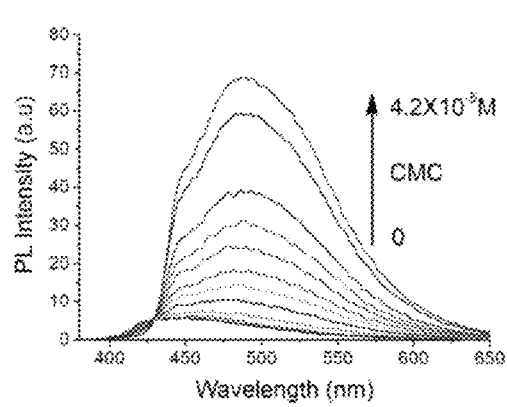
FIG. 12 shows the fluorescence spectra of N-OPE-2 upon addition of CMC.

N-OPE:CMC complexes can be formed by adding small aliquots of CMC to aqueous solutions containing the N-OPE compound. For both N-OPE-1 and N-OPE-2 there are similar striking changes in both the absorption and fluorescence spectra upon addition of small aliquots of CMC to aqueous solutions as shown in FIGS. 9-12. FIG. 9 shows the absorption spectra of N-OPE-1 upon addition of various CMC concentrations. [N-OPE-1]=1.5×10$^{-5}$M. FIG. 10 shows the fluorescence spectra of N-OPE-1 upon addition of CMC. [N-OPE-1]=1.5×10$^{-5}$ and [CMC]=5.0×10$^{-5}$ M. FIG. 11 shows the absorption spectra for N-OPE-2 upon addition of CMC. [N-OPE-2]=1.5×10$^{-5}$ M. FIG. 12 shows the fluorescence spectra of N-OPE-2 upon addition of CMC. [N-OPE-2]=1.5×10$^{-5}$ and [CMC]=0-4.2×10$^{-5}$M. Both excitation and emission slits are 2.5 nm. Excitation wavelength for N-OPE-1 is 355 nm and for N-OPE-2 is 375 nm. For both N-OPEs there are several isosbestic points in the absorption spectra as the two bands in the absorption for water alone are replaced by a spectrum of the N-OPE:CMC having two bands at longer wavelength. For both N-OPEs the fluorescence also undergoes a red shift and increase in intensity as aliquots of CMC are added, finally leveling off at moderate concentrations (greater than 1 mM) of CMC. The increase in fluorescence of N-OPE-1 is at least three-fold while that for N-OPE-2 is at least 14-fold. The clean spectral evolution and structured spectrum for the N-OPE-CMC complexes suggest that the N-OPEs are assembling on the planar sheets of CMC as discrete units. We suggest these spectral shifts could be attributed to the formation of dimers, most likely extended linearly as "J" type dimers. The spectral shifts seem reasonable for a linear dimer; we note that the absorption spectrum of N-OPE-1:CMC is slightly red-shifted compared to N-OPE-2 in water alone. Comparing the estimated length of the linear N-OPE "rigid rod" the "conjugation length" of a linear N-OPE-1 dimer should be slightly longer than that of N-OPE-2. The spectral shifts are also consistent with "planarization" of the chromophores for a monomer assembling on the scaffold.

The N-OPE-CMC complexes can also be generated by addition of small aliquots of the N-OPE to a fixed concentration of CMC. When this was done with N-OPE-1, the very lowest concentrations of N-OPE-1 produced absorption indicative of a mixture of monomer and complex; as the (N-OPE-1) increased the spectra indicated only the complex was being formed on the CMC until a limiting ratio of (N-OPE-1):(moles of CMC polymer repeat units) (CMC-PRU)=18:50 is reached. As additional N-OPE-1 is added only the monomer spectrum is observed to grow indicating that saturation of the CMC scaffold has occurred. For N-OPE-2 with CMC, addition of even the lowest concentrations of N-OPE-2 result in the spectral signature of what we suggest should be a "J" dimer and the limiting concentration ratio of (N-OPE-2):(CMCPRU)=14:50. Here again as additional N-OPE-2 is added only the monomer spectrum increases.

We also examined the interactions between CMA and the two N-OPE in aqueous solution. Addition of CMA to an aqueous solution of N-OPE-1 does not generate a spectrally observable aggregate. A monotonic decrease in the absorption of N-OPE-1 is observed (275-380 nm) upon addition of aliquots of CMA with the only increase in absorption being a small shoulder near 400 nm. There is a small increase in fluorescence and then a subsequent decrease with addition of CMA. In contrast, when aliquots of CMA are added to a solution of N-OPE-2 an intense red-shifted absorption grows in, very similar to that observed for CMC and a corresponding increase and red-shift in fluorescence. The fluorescence of the N-OPE-2:CMA complex is more than ten-fold increased compared to N-OPE-2 in water.

The isosbestic points obtained in the association of the N-OPE with CMC and CMA suggest that a two-state model can be used and we assume that the equilibrium is for the reaction:

Figure 13:
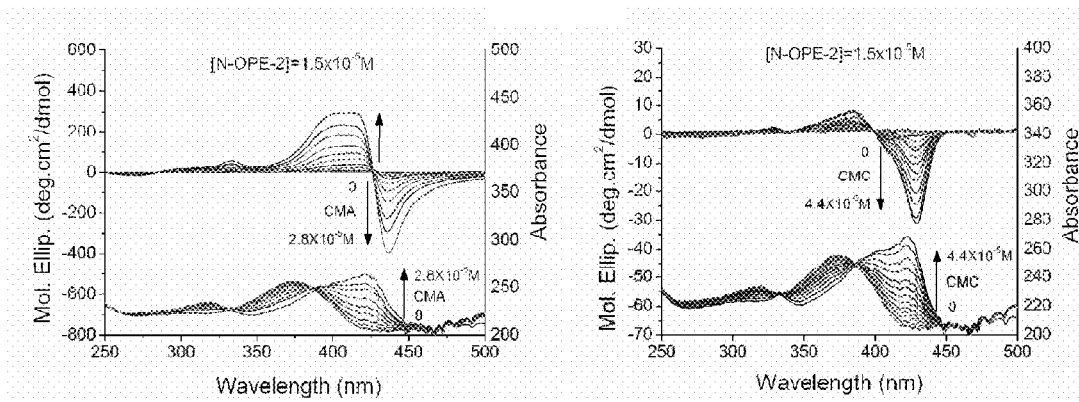
FIG. 13 shows the circular dichroism spectra of N-OPE-2 upon addition of CMA.
Figure 14:
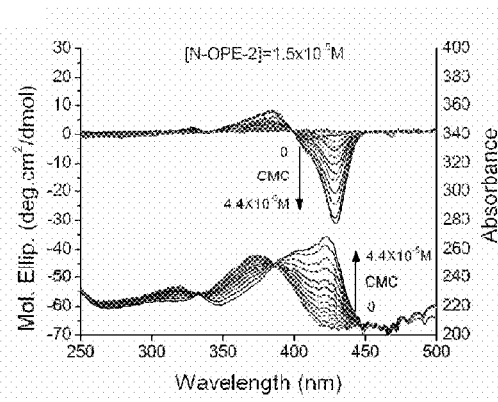
FIG. 14 shows the circular dichroism spectra of N-OPE-2 upon addition of CMC.

2N-OPE+CMC(or CMA)=CMC:(N-OPE)2 where K=[CMC:(N-OPE)2]/(N-OPE)2(CMC). Binding constants (assuming that an N-OPE dimer is formed in each case) can be estimated from a determination of the individual absorbances of the two species following a treatment for a similar two-state system developed by Pasternack and coworkers. See, e.g., Pasternack, R. F.; Goldsmith, J. I.; Szep, S.; Gibbs, E. J. *Biophys. J.* 1998, 75, 1024-1031, which is incorporated by reference. The absorbances, extinction coefficients and concentrations were determined and used to estimate K. The obtained values (K=1.3×1010 M-2 for CMC:(N-OPE-2)2 and K=2.4×1012 M-2 for CMA:(N-OPE-2)2; values for the CMC complex with N-OPE-1 are less accurate and slightly lower) indicate that the complexes are tightly bound. For N-OPE-2 addition of either CMC or CMA results in an induced circular dichroism (CD) spectrum as shown in FIGS. 13 and 14. FIG. 13 shows the circular dichroism spectra of N-OPE-2 upon addition of CMA. [N-OPE-2]=1.5×10$^{-5}$ and [CMA]=0-2.8×10$^{-5}$ M. FIG. 14 shows the circular dichroism spectra of N-OPE-2 upon addition of CMC. [N-OPE-2]=1.5×10$^{-5}$ and [CMC]=0-4.4×10$^{-5}$ M. The induced CD observed for N-OPE-2 and CMA is strong and biphasic with a change in phase of the induced CD exactly corresponding to the maximum in the J-dimer absorption. This is similar to what was observed for CMA complex formation with a cyanine dye J-aggregate reported earlier and attributed to a cooperative self-assembly into a helical arrangement for the host-guest complex. See, e.g., Kim, O. K.; Je, J.; Jernigan, G.; Buckley, L.; Whitten, D. *J. Am. Chem. Soc.* 2006, 128, 510-516, which is incorporated by reference.

A similar structure may thus be reasonable for the CMA:N-OPE-2 complex. For the N-OPE-2 complex with CMC, the induced CD spectrum is much weaker and contains two bands corresponding to different absorptions: the longer wavelength band (negative) overlaps the transition we attribute to a J-dimer of N-OPE-2 while the shorter wavelength band (positive) overlaps the monomer of N-OPE-2.

Figure 15:
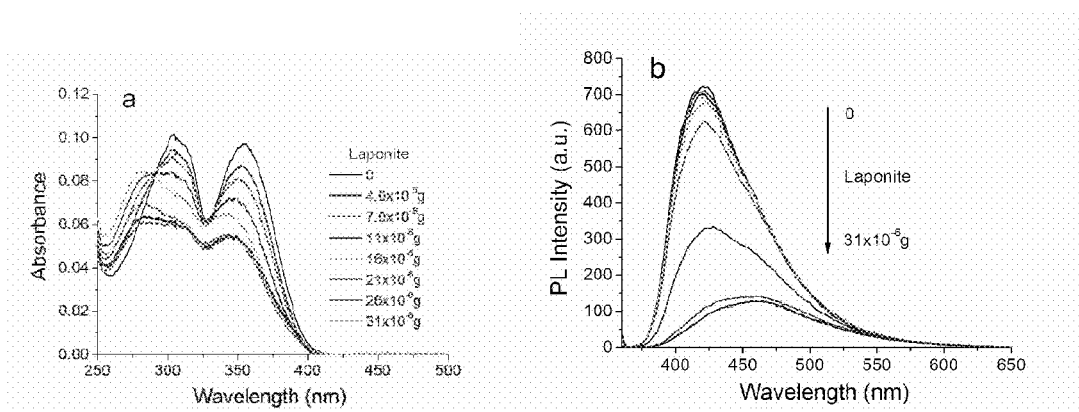
FIG. 15 shows the absorption spectra of N-OPE-1 upon addition of Laponite.
Figure 16:
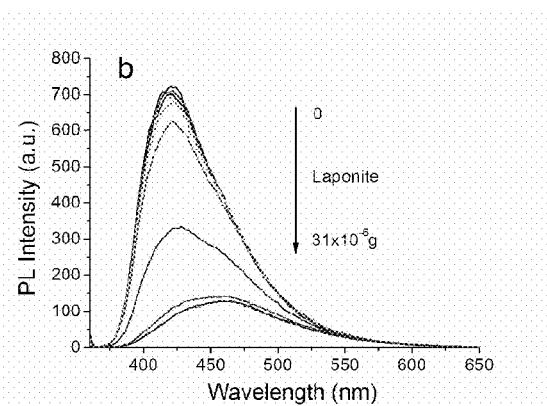
FIG. 16 shows the fluorescence spectra of N-OPE-1 upon addition of Laponite.
Figure 17:
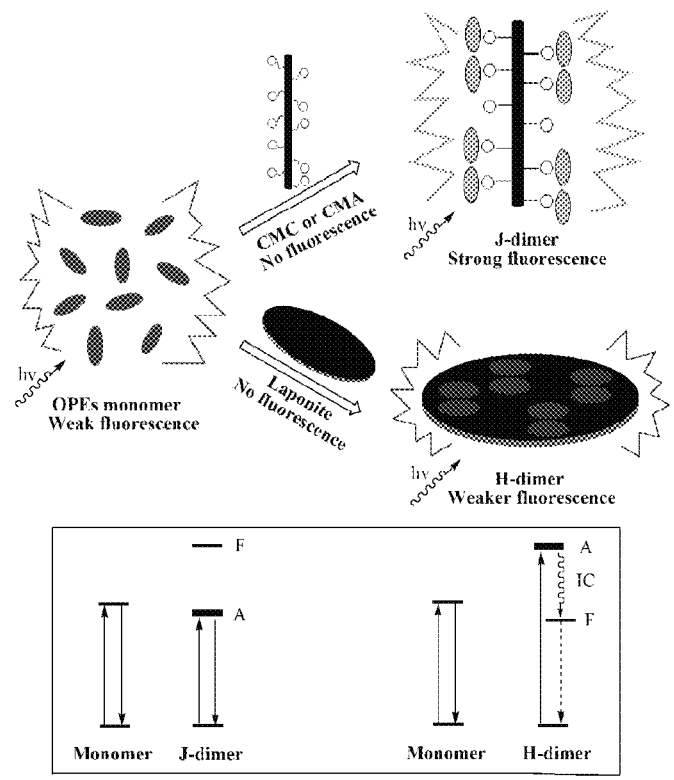
FIG. 17 is a schematic of a proposed self-assembly processes occurring with the OPE.

Both N-OPEs were found to undergo very different spectral changes when aqueous solutions were treated with aliquots of nanoparticulate Laponite clay. For N-OPE-1 the two banded spectrum in the near UV decreased in intensity with addition of Laponite and shifted to shorter wavelengths (see FIGS. 15 and 16 where FIG. 15 shows the absorption spectra of N-OPE-1 upon addition of Laponite [N-OPE-1]=3.0×10$^{-6}$ and FIG. 16 shows the fluorescence spectra of N-OPE-1 upon addition of Laponite [N-OPE-1]=3.0×10$^{-6}$, both excitation slits are 5.0 nm) while the fluorescence decreased in intensity and was observed to undergo a red-shift in the maximum from 420 nm to 450 nm. For N-OPE-2 a similar decrease and blue-shift in the monomer absorption was observed, however a clear shoulder at longer wavelengths is observable and the fluorescence increased with addition of Laponite. These spectral changes are consistent with formation of an H-aggregate or more likely an H-dimer in both cases. See e.g., Song, X. D.; Perlstein, J.; Whitten, D. G. *J. Am. Chem. Soc.* 1997, 119, 9144-9159, which is incorporated by reference. Based on estimates of the area of N-OPE-1 and N-OPE-2 and the surface area of Laponite we calculate that coverage of the clay by N-OPE-1 reaches a limiting value at ~45% coverage and for N-OPE-2 the limiting value is approximately 100%. A schematic of the proposed self-assembly processes occurring with the N-OPE is shown in FIG. 15, where F denotes a forbidden excited state, A denotes an allowed excited state and IC denotes internal conversion.

In studies with cationic PPE polymers we have found that their fluorescence is strongly quenched by the anionic electron acceptor 9,10-anthraquinone-2,6-disulfonic acid (AQS) for both solution phase polymer and microsphere-supported physisorbed polymers. The fluorescence quenching is attributed to ground state association of the AQS with the polymer by a combination of Coulombic and hydrophobic effects and a rapid electron transfer quenching of the excited state. For the PPE polymers there is normally very little change in the polymer absorption spectrum. For both N-OPE-1 and N-OPE-2 addition of AQS to solutions of the oligomers results in both a strong spectral change and efficient quenching of the oligomer fluorescence. The absorption spectral changes that occur when AQS is added to solutions of the N-OPE are almost identical to those observed when CMC is added to the compounds and indicates that the relatively small molecule AQS is also providing a template onto which the N-OPE can form a J-dimer. The spectrum of the AQS is relatively little perturbed by association with the N-OPE suggesting that the ground state charge transfer interaction may be very weak. In contrast to the results when the N-OPEs are added to CMC and CMA, the formation of the J-dimers on AQS is accompanied by quenching of the oligomer fluorescence and there is no fluorescence from the templated J-dimers of the N-OPE when dimer formation is complete. Stern-Volmer quenching constants can be obtained for the early (low (AQS)) stages of the complex formation/quenching and the values obtained ($K_{SV}$=6.7×103 M−1 and 8.1×104 M−1 are reasonable based on a largely Coulombic association between multiply charged cations and anions.

The results suggest that the cationic N-OPE's readily participate in strong host-guest interactions with anionic scaffolds and that this interaction may be quite general. The formation of linear "J-dimers" results in substantial absorption and fluorescence spectral shifts to lower energies that suggest an effective increase in conjugation length. Our results with the first two members of the series suggest that the magnitude of these effects and the formation of dramatically shifted supramolecular complexes may be enhanced as the length of the N-OPE is extended to the next members of the series (i.e., N-OPE-3 and N-OPE-4).

Figures 18, 19:
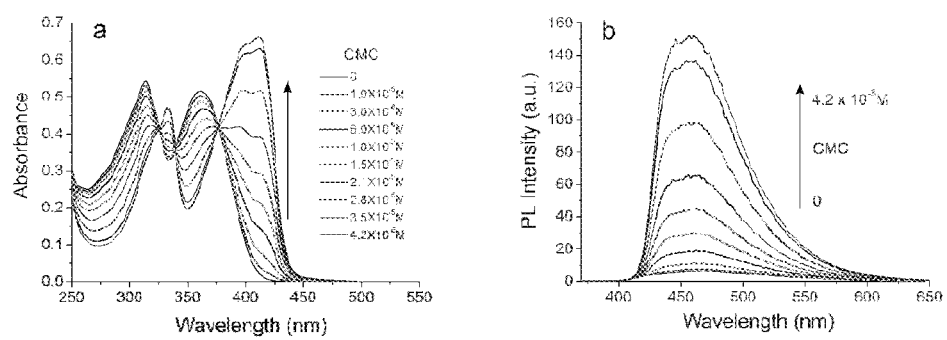
FIG. 18 shows the absorption spectral changes of S-OPE-1 (COOEt) upon addition of aliquots of CMC to an aqueous solution of S-OPE-1 (COOEt).
FIG. 19 shows fluorescent spectral changes under the same conditions.

Self-assembly is not limited solely to the non-symmetrical N-OPE compounds. The three cationic oligomers, S-OPE-1 (H), N-OPE-1 and S-OPE-1 (COOEt) all show striking changes in absorption and fluorescence when CMC (Sigma Aldrich, degree of carboxyl substitution (DS)=0.7) is added to aqueous solutions (oligomer concentration ~15 mM) in the mM concentration range. FIG. 18 shows the absorption spectral changes of S-OPE-1 (COOEt) upon addition of aliquots of CMC to an aqueous solution of S-OPE-1 (COOEt). FIG. 19 shows fluorescent spectral changes under the same conditions. Similar spectral changes, but with less pronounced red shifts, are observed over the same concentration range for S-OPE-1 (H) and N-OPE-1. Interestingly, there are no changes observed when a similar study is made for S-OPE-1 (COO—) with CMC at near neutral pH. The changes that occur for S-OPE-1 (H), N-OPE-1 and S-OPE-1 (COOEt) (sharp, red shifted absorption spectra, isosbestic points maintained throughout the CMC addition and red-shifted fluorescence) are consistent with an extension of effective conjugation for the oligomers on the carboxylate decorated surface of the CMC. The fluorescence quantum efficiency of the oligomer: CMC complex shows a dramatic increase for S-OPE-1 (COOEt) (more than 18-fold), a strong increase for N-OPE-1 and very little change for S-OPE-1 (H). The absorption and fluorescence maxima for N-OPE-1/CMC, S-OPE-1(H)/CMC and S-OPE-1 (COOEt)/CMC are listed in Table 3.

TABLE 3

Fluorescence Quantum Efficiencies

|  | Abs. (nm) | Em. (nm) | $\phi_f$ in H$_2$O |
|---|---|---|---|
| N-OPE-1/CMC[b] | 325, 381 | 472 | 0.34 ± 0.004 |
| S-OPE-1 (H)/CMC[c] | 308, 318, 367 | 423 | 0.81 ± 0.017 |
| S-OPE-1 (COOEt)/CMC | 333, 412 | 458 | 0.39 ± 0.023 |

The spectroscopic behavior of S-OPE-1 (COOEt) with CMC is reminiscent of the formation of cyanine J-aggregates templated on carboxymethylamylose and CMC. See, e.g., Kim, O.-K.; Je, J.; Jernigan, G.; Buckley, L.; Whitten, D. G. J. Am. Chem. Soc. 2006, 128, 510-516; and Whitten, D. G.; Achyuthan, K. E.; Lopez, G. P.; Kim, O.-K. Pure Appl. Chem. 2006, 78, 2313-2323. The increase in effective conjugation could be attributed either to planarization or to formation of J-dimers. Structurally similar OPE's have been investigated in organic solvent systems; although there is indicated to be little barrier to rotation of the phenyl rings from a totally coplanar structure, the completely planar system is estimated to be a slight energy minimum. Additionally in this experimental and computational study the absorption spectrum calculated for a completely planar structure is similar to those shown in FIGS. 18 and 19 and Table 2 and also to that found for the N-OPE. As with other cases of host-guest complex formation in aqueous media, the formation of a planarized monomer or J-dimer of the oligomers on CMC is likely attributable to a combination of favorable Coulombic and hydrophobic interactions between the host and guest with favorable molecular topographies either pre-existing or induced during the complex formation. The failure of S-OPE-1 (COO—) to interact with CMC is not surprising since it should be a zwitterion at neutral pH and thus there should be no Coulombic attraction towards the CMC host.

The sharply reduced fluorescence of the two ester containing oligomers, N-OPE-1 and S-OPE-1 (COOEt) in aqueous solution, compared to methanol, is remarkable and unprecedented for simple aromatic esters. While we do not yet know the origin of these effects, we have found that other S-OPE-1 with different substituents (X=NH2, —COCH3) exhibit similar reduced fluorescence in water.

The strong spectral red shifts in both absorption and fluorescence coupled with the increase in fluorescence efficiency upon complexation with CMC, suggests that S-OPE-1 (COOEt) and other oligomers having extended p conjugation may be useful in sensing applications similar to those already demonstrated for certain cationic cyanines and anionic biopolymers such as hyaluronic acid and DNA. It is striking that excitation of S-OPE-1 (COOEt) in water at 412 nm results in an increase from essentially no fluorescence at 470 nm to a very strong fluorescence easily detectable at micromolar concentrations of CMC repeat units. Since oligomers having extended symmetrical structures from the structure of 2 can be readily generated with a variety of substituents and other structural features, it should be possible to generate a versatile library of dyes and fluorescent probes extending into the visible region.

As stated above, at least some of the compounds described herein are useful in sensing applications. One particularly useful sensing application is DNA detection. Accordingly, the present disclosure provides a novel DNA detection mechanism. According to various embodiments, this detection mechanism does not involving labeling of the DNA and furthermore, is able to differentiate between single and double stranded DNA.

Specifically, some OPEs display circular dichroism (CD) signals when bound to either single stranded (ss) or double stranded (ds) DNA. Moreover, in some cases, the signals are noticeably different depending on whether the OPE is bound to ds or ss DNA. Accordingly, this signal differential can be exploited to detect hybridization events.

Figure 20:
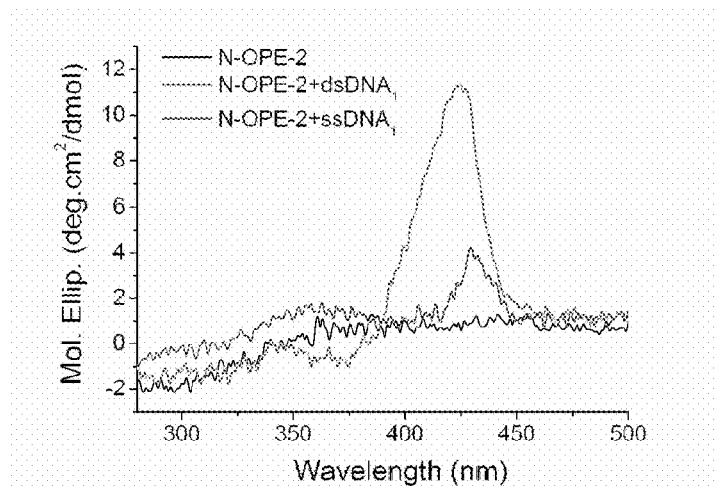
FIG. 20 shows the circular dichroism spectra of N-OPE-2 before and after addition of dsDNA or ssDNA.

As an example, N-OPE-2 and S-OPE-1 (COOEt) provide useful circular dichroism (CD)-based detection mechanisms because they display a detectable CD signal when bound to DNA. Furthermore, the signal varies noticeably, depending on whether the OPE is bound to ds or ss DNA. In an example, CD experiments were carried out as follows: ssDNA ([ssDNA]=6.9×10$^{-6}$M) or dsDNA ([dsDNA]=6.9×10$^{-6}$M) was added to a solution of N-OPE-2 ([N-OPE-2]=1.5×10$^{-5}$ M) in 220 μL phosphate buffer (25 mM, pH 7.4). The solution was then incubated for 30 s. The CD spectra were measured at room temperature. The CD spectra (FIG. 20, where [N-OPE-2]=5.0×10$^{-6}$ M, [dsDNA]=[ssDNA]=1.1×10$^{-6}$ M.) obtained showed that the N-OPE-2:ssDNA complexes produced a strong positive CD signal, while the N-OPE-2:dsDNA had a detectable, but much weaker signal. The N-OPE-2 can form complexes with dsDNA along the two phosphate backbones, so it is possible that the CD signal of N-OPE-s:dsDNA complexes is obstructed. Accordingly, the differential in CD signal between ssDNA and dsDNA complexes can be exploited to detect hybridization events.

Similarly, some OPEs display detectable fluorescence when bound to ds or ss DNA. Again, some compounds reflect a noticeable difference in the fluorescence spectra when bound to ds versus ss DNA.

As an example, N-OPE-2 provides a useful fluorescence-based detection mechanism because it displays a detectable fluorescence signal when bound to DNA. Again, the signal varies noticeably, depending on whether the N-OPE-2 is bound to ds or ss DNA. However, in this case, the signal is stronger when the N-OPE-2 is bound to dsDNA. The fluorescence experiments are performed as follows. A 2 mL of phosphate buffer solution (25 mM, pH 7.4) was added to 10 µL N-OPE-2 ([N-OPE-2]=5.0×10$^{-6}$ M) at room temperature. Either ssDNA or dsDNA was then added to the N-OPE-s solution successively. The fluorescence spectra were measured after mixing for 30 s. When the concentrations of dsDNA and ssDNA are 1.1×10$^{-6}$ M, the fluorescence intensity of the complexes of N-OPE-2/dsDNA is much greater than that of the complexes of N-OPE-2/ssDNA.

Figure 21:
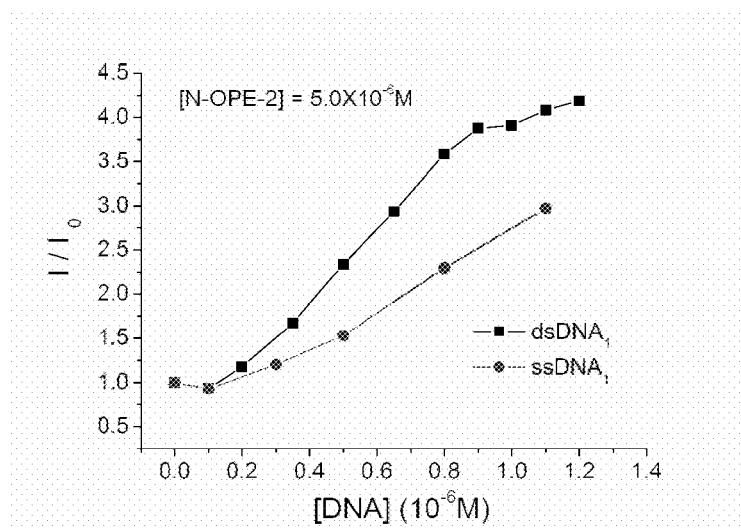
FIG. 21 depicts $I_{signal}/I_{blank}$ as a function of DNA concentration in phosphate buffer.

FIG. 21 depicts $I_{signal}/I_{blank}$ as a function of DNA concentration in phosphate buffer (25 mM, pH 7.4 [N-=OPE-2] =5.0×10-6 M. The excitation wavelength is 378 nm. It can be seen that the plot for N-OPE-2/dsDNA is higher than for N-OPE-2/ssDNA. This is because the interactions between N-OPE-2 and dsDNA are stronger than that of N-OPE-2 and ssDNA, since N-OPE-2 can more easily form complexes with dsDNA. Accordingly, this differential in binding strength between dsDNA and ssDNA can be exploited to detect DNA hybridization without labeling the DNA, simply by detecting a differential in fluorescence spectra.

As described in greater detail below, the OPEs described herein have varying levels of both dark and light-induced biocidal activity. Penetration of the bacterial membrane and binding of OPEs with DNA may provide paths for this activity. Accordingly, in yet another embodiment, the present disclosure provides novel biocides formed from the OPEs described herein.

The OPEs described herein have been synthesized and studied as dark and light activated biocides towards a Gram negative bacterium, *Pseudomonas aeruginosa* Strain PAO1. The unsymmetrical compounds, N-OPE-1, N-OPE-2 and N-OPE-3, terminated in each case by a carboxy ester or carboxylic acid, are active biocides both in solution and attached to surfaces. N-OPE-1 is active as a biocide under short term irradiation with near ultraviolet light, but relatively inactive when exposed to the bacteria in the dark for periods of up to one hour. In contrast, N-OPE-2 and N-OPE-3 are active against bacteria both in the dark and in the light. N-OPE-1 has been attached to surfaces by covalent linkage. This has been accomplished for both micron sized glass beads and glass slides. The bead-grafted N-OPE-1 has been studied as a biocide and has been found to exhibit the ability to capture *Pseudomonas a.* in a dark process (relatively little killing of the bacteria in the dark over ~15 minutes,) and to exhibit good biocidal activity on irradiation with 365 nm uv. The biocidal activity of bead crafted N-OPE-1 is comparable or stronger than that of solution phase N-OPE-1. We anticipate that bead and planar surface grafted N-OPE-n (n>1) will exhibit strong dark and light-induced biocidal activity.

Three S-OPE-n (x=H) have been studied as biocides with suspensions of *Pseudomonas* and it has been found that the light-activated biocidal activity increases in the series S-OPE-1 (x=H)<S-OPE-2 (x=H). Dark biocidal activity (much slower) was observed for S-OPE-2 (x=H) and S-OPE-3 (x=H). Biocidal activity is comparable for members of the N-OPE-n series and for the S-OPE-n (x=H).

S-OPE-EO has remarkable biocidal activity in the dark and upon uv irradiation against Gram positive *Bacillus atrophaeus*. Samples of the bacterial exposed to S-OPE-EO in the dark show several log kills following 6 hour exposure (a live control shows very little killing). A similar sample irradiated with 365 nm uv light shows almost the same level killing after 30 minutes.

Previous studies have shown that certain conjugated polyelectrolytes exhibit visible light-activated biocidal activity against gram-negative and gram-positive bacteria such as *E. coli* and *B. anthracis*. In these studies it was found that exposure of solutions of the polymer to suspensions of bacteria results in coating of the cationic polymer onto the surface of the bacteria. Irradiation of the polymer-coated bacteria results in killing of the bacteria. Subsequent investigations have shown that these same polymers can be effective at killing bacteria when incorporated into coatings either by physisorbing the polymer to a surface or by grafting the polymer covalently to a surface. The polymer coatings are active in trapping bacteria in the dark and the entrapped bacteria can be killed slowly in the dark or much more rapidly by irradiation with visible light. Recent experiments have demonstrated that the light activated biocidal activity is initiated by interfacial sensitization of a reactive oxygen intermediate. Singlet oxygen is certainly the initially formed reactive oxygen intermediate but more corrosive species may be generated in subsequent steps. The OPEs of the present disclosure can be formed into biocidal polymers using the above-described self-assembly, or other suitable, techniques.

Furthermore, much recent work has been devoted to the development of materials whose properties can be altered drastically by relatively small changes in properties such as temperature, pressure, solution or suspension properties (including but not limited to pH); these "stimuli responsive materials" (SRM) are often prepared as polymers or as surfaces prepared from components that can be covalently linked or self assembled on surfaces. Smart polymers that have found use in biotechnology and medicine have been described by I Yu Galaev in Russian Chemical Reviews 64: 471-489 (1995); A. S. Hoffman in Clinical Chemistry 46:1478-1486 (2000) and H. G. Schild, *Prog. Polym. Sci.* 17, 163 (1992), incorporated herein by reference.

Prominent examples of SRMs include poly (N-isopropylacrylamide) (PNIPAAM) and oligo-ethylene glycol oligomers terminated with a thiol (OEG). The former can be grown from a surface by attaching an initiator monomer to a surface and following this with in situ polymerization. Through an ATRP process; the thickness of the resulting film can be controlled as a function of incubation time at a fixed catalyst and monomer concentration. The OEGs can be attached to a surface (usually Au) by covalent assembly as a self-assembled monolayer (SAM). For surfaces coated with either PNIPAAM or OEG there is a strong temperature dependence of the film properties. In both cases, films formed from these materials in contact with an aqueous solution exist as hydrated, expanded films at low temperatures that are relatively unreactive and non-adsorbtive towards various biological species including proteins, cells, bacteria, viruses, and the like. Above a specific lower critical solution temperature (LCST) the films contract, releasing water and become very hydrophobic. At temperatures higher than the LCST films from either SRM become thinner and strongly attract proteins, cells and other biological species that do not bind below the LCST.

Figure 22:
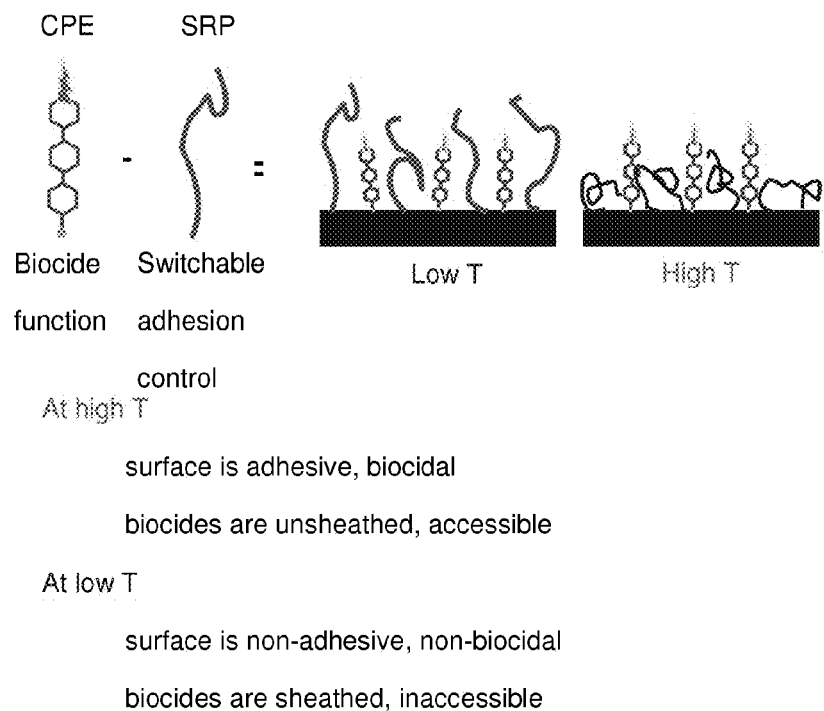
FIG. 22 shows exemplary features of one example of a two-component bi-functional film according to an embodiment of the present disclosure.

According to yet another embodiment, the present disclosure provides films and assemblies containing both SRM components and oligomeric units of the conjugated OPEs described above. Exemplary features of one example of these two-component bi-functional films are shown in FIG. 22. In general, these assembles provide a novel functional material that can be switched between active and inactive forms wherein, in the active form, the material is able to capture a biological species of interest and, in the inactive form, the material is able to release the biological species. In some embodiments the material can be switched between active and inactive forms repeatedly, allowing for reuse of the same material. Films containing these two functional components can be readily prepared by covalent synthesis or by a self assembly process employing a mixture of individual SRM and OPE thiols.

Viewing FIG. 22, it can be seen that at low temperatures an OPE of appropriate length is buried amidst the expanded form of the SRM and inaccessible to any biological species (such as a protein, cell, bacteria, virus, etc.) present in the aqueous media. Moreover, these species are not attracted to the surface and do not associate with it. However, as the temperature is elevated above the LCST, contraction of the SRM component "unsheathes" the OPE. Both components are now hydrophobic and strongly attractive. Accordingly, the unsheathed OPE is able to form a complex with the biological species.

Accordingly, in one embodiment, the presently described structure can form a reusable biocidal material. Under low temperatures the antimicrobial activity of the OPE is masked by the extended SRMs and therefore inactive. As stated above, elevation of the temperature above the LCST unsheathes the OPE, which is then allowed to form a complex with, thereby trapping, the bacteria. The OPE's biocidal activity is then exploited to inactivate, kill or destroy the trapped species, under either dark conditions or under uv light irradiation. Following destruction of the pathogen, the film will typically be contaminated with debris from the killed bacteria or cell. Returning the film to temperatures lower than the LCST results in expansion of the SRM, forcing the debris away from the OPEs. The result is a self-cleaning, reusable, biocidal film.

Examples of other practical uses for these mixed films include employing them as an active sensor which can be monitored by steady state fluorescence or by laser interferometry. The attachment of protein, cells or bacteria to the surface can be detected, for example, by the monitoring irradiation.

Figure 23:
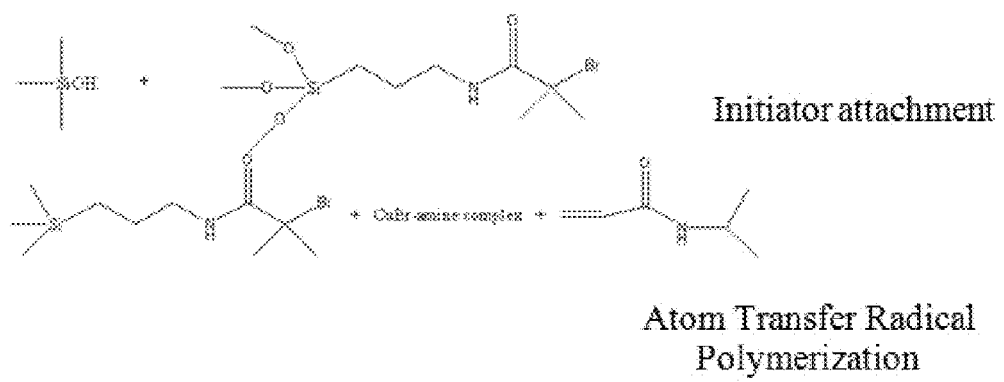
FIG. 23 depicts a method of synthesis of PNIPAAM by monomer polymerization onto an initiator functionalized surface.

The present disclosure further provides methods of manufacturing the functional materials described herein. Thiol terminated OEG derivatives are commercially available in a wide range of structures. A method of synthesis of PNIPAAM by monomer polymerization onto an initiator functionalized surface is shown in FIG. 23.

Synthesis of a wide variety of OPE units is described above. The OPE derivatives can be concerted to the carboxylic acid which can be then surface linked to an amine functionalized surface or converted to a thiol and attached to gold at the same time as an OEG derivative.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications. The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

What is claimed is:
1. A cationic oligo phenylene ethylene (OPE) having the structure:

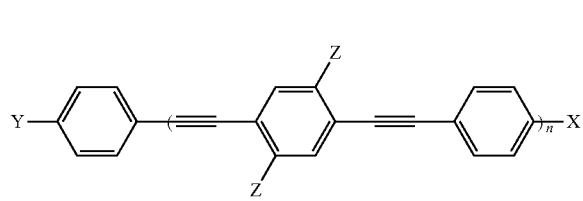

Where:
X=COOEt
Y=H
Z=OCH$_2$CH$_2$CH$_2$N(CH3)$_3{}^+$ and
n is selected from the group consisting of numbers between 1 and 10
or
X=Y and is selected from the group consisting of H, CO$_2$Et, COO$^-$, NH$_2$ and COCH$_3$ $Z=OCH_2CH_2CH_2N(CH_3)_3^+$ and n is selected from the group consisting of numbers between 1 and 10 or $X=Y=OCH_2CH_2CH_2N(CH_3)_3^+$ and $Z=H$ and $n=1$.

2. The cationic OPE of claim 1 where
$X=COOEt$
$Y=H$
$Z=OCH_2CH_2CH_2N(CH_3)_3^+$ and
n is selected from the group consisting of numbers between 1 and 10.

3. The cationic OPE of claim 1 where
$X=Y$ and is selected from the group consisting of H, $CO_2Et$, $COO^-$, $NH_2$ and $COCH_3$
$Z=OCH_2CH_2CH_2N(CH_3)_3^+$ and
n is selected from the group consisting of numbers between 1 and 10.

4. The cationic OPE of claim 1 where
$X=Y=OCH_2CH_2CH_2N(CH_3)_3^+$ and
$Z=H$ and
$n=1$.

5. The cationic OPE of claim 1, wherein the cationic OPE exhibits biocidal activity.

6. The cationic OPE of claim 5, wherein the biocidal activity is activated by exposure to light.

7. The cationic OPE of claim 6, wherein the cationic OPE is incorporated into a functional material.

8. The cationic OPE of claim 7 wherein the functional material further incorporates a stimuli responsive polymer.

9. The cationic OPE of claim 8 wherein the functional material can be switched between first and second forms upon exposure to an external stimulus and wherein in the first form the functional material is able to capture pathogens and in the second form the functional material is able to release inactivated pathogen or pathogen debris.

10. A functional material incorporating the cationic OPE of claim 1,
wherein the functional material can be switched between a first form and a second form upon exposure to an external stimulus and wherein in the first form the functional material is able to form a complex between the cationic OPE and a biological species of interest and in the second form the functional material is able to release the biological species of interest.

11. The functional material of claim 10 wherein the external stimulus is selected from the group consisting of exposure to light, an alteration in temperature, an alteration in pressure, an alteration in solution and an alteration in suspension properties.

12. The functional material of claim 10 further comprising a pathogen detection mechanism.

13. A material comprising a stimuli responsive polymer and the cationic OPE of claim 1,
wherein the material is configured to attract a target and wherein under a first condition the stimuli responsive polymer is configured to sheathe the cationic OPE and prevent the cationic OPE from associating with the target and under a second condition the stimuli responsive polymer is configured to unsheathe the cationic OPE, thereby making the cationic OPE accessible for association with the target.

14. A method comprising exposing a target biological species to the cationic OPE of claim 1,
so as to form an OPE:biological species complex.

15. The method of claim 14 wherein the cationic OPE is incorporated into a functional material that can be switched between a first form and a second form upon exposure to an external stimulus and wherein an active first form of the functional material is able to capture pathogens and in an inactive second form the functional material is able to release inactivated pathogen or pathogen debris.

16. The method of claim 14 wherein the target biological species is DNA.

17. The method of claim 14 wherein the target biological species is a pathogen.

18. The method of claim 17 further comprising irradiating the OPE:biological species complex with UV light.

19. A method comprising:
providing a functional material comprising a stimuli responsive polymer and the cationic OPE of claim 1,
wherein the functional material can be switched between first and second forms upon exposure to an external stimulus and wherein in the first form the functional material is able to capture pathogens and in the second form the functional material is able to release inactivated pathogen or pathogen debris;
exposing the functional material in the first form to a pathogen so that the functional material captures the pathogen;
altering the pathogen while it is captured by the functional material; and
returning the functional material to the second form to release the altered pathogen.

20. The method of claim 19 further comprising irradiating the functional material with UV light.

* * * * *